United States Patent

Tabata et al.

[11] Patent Number: 5,712,306
[45] Date of Patent: Jan. 27, 1998

[54] PHYSIOLOGICALLY ACTIVE SUBSTANCES PF1092A, PF1092B AND PF1092C, AND CONTRACEPTIVES AND ANTICANCER DRUGS CONTAINING THE SAME AS ACTIVE INGREDIENTS

[75] Inventors: Yuji Tabata; Masahiro Hatsu; Naoko Miike; Takashi Yaguchi; Ayako Someya; Yasushi Kurata, all of Kanagawa, Japan

[73] Assignee: Meiji Seika Kaisha, Ltd., Tokyo, Japan

[21] Appl. No.: 585,411

[22] Filed: Jan. 11, 1996

[30] Foreign Application Priority Data

Jan. 17, 1995 [JP] Japan ................................. 7-020860

[51] Int. Cl.$^6$ .......................... A61K 31/34; C07D 307/77
[52] U.S. Cl. ............................................. 514/468; 549/299
[58] Field of Search ............................. 514/468; 549/299

[56] References Cited

PUBLICATIONS

K. Yamakawa et al., "Studies on the Terpenoids and Related Aclicyclic Compounds . . . and (+−)-Furanoligularanone", *Chemical and Pharmaceutical Bulletin*, 28:11:3265–3274, (1980).

I.S. Levina et al., "Relationship Between Structure and Mode of Action of 16α, 17α-cycloalkanoprogesterones (pregna-D'-pentaranes)", *Chemical Abstracts*, 98:21:118, col. 2, (1983).

*Primary Examiner*—Ba K. Trinh
*Attorney, Agent, or Firm*—Sughrue, Mion, Zinn, Macpeak & Seas, PLLC

[57] ABSTRACT

This invention provides novel physiologically active substances PF1092A, PF1092B and PF1092C, which can inhibit binding of progesterone to progesterone receptor.

These substances were obtained by culturing a fungal microorganism belonging to the genus Penicillium using a medium containing ordinary nutrients for microorganisms and isolating the physiologically active substances PF1092A, PF1092B and PF1092C from the resulting culture mixture by means of solvent extraction, silica gel column chromatography, and the like. Molecular formulae of the novel physiologically active substances PF1092A, PF1092B and PF1092C are $C_{17}H_{20}O_5$, $C_{17}H_{20}O_5$ and $C_{15}H_{18}O_4$, respectively.

5 Claims, 9 Drawing Sheets

PHYSIOLOGICALLY ACTIVE SUBSTANCES PF1092A, PF1092B AND PF1092C, AND CONTRACEPTIVES AND ANTICANCER DRUGS CONTAINING THE SAME AS ACTIVE INGREDIENTS

FIELD OF THE INVENTION

This invention relates to novel physiologically active substances PF1092A, PF1092B and PF1092C, or salts thereof, which are useful as contraceptives or therapeutic drugs for certain forms of hormone dependent cancer of the breast, ovaries, uterus and endometrium, and to a process for the production thereof.

BACKGROUND OF THE INVENTION

Progesterone, which is a sex hormone, is an effective gestagen biologically synthesized in endocrine organs. It is an intermediate of various steroid hormones biologically synthesized from cholesterol, and its main secretion sources are corpus luteum and placenta. In the uterus and mammary gland, progesterone receptors are induced by pretreatment of estrogen, and progesterone is secreted from corpus luteum appeared after ovulation and renders possible implantation of fertilized egg in the uterus. Because of such a function, inhibiting substances of the progesterone-progesterone receptor binding (progesterone receptor antagonist) are used as contraceptives.

In the treatment for breast cancer, the ablative surgery such as oophorectomy and adrenalectomy have been carried out actively since the late nineteenth century. Thereafter, based on the progress in studies on the structures and physiological functions of sex hormones such as estrogen and progesterone, and their receptors, the antiestrogen tamoxifen was found (Wiseman, Tamoxifen, published by John Wiley & Sons, England, 1994), and the endocrine therapy of breast cancer was drastically changed by this discovery from the ablative surgery to internal endocrine therapy. In addition, a synthetic gestagen MPA (medroxyprogesterone acetate) (Y. Iino etal., Jpn. J. Breast Cancer, vol. 1, pp. 201–213, 1986) has been put into practical use, and LH-RH (luteinizing hormone releasing hormone) agonist and aromatase inhibitor have been newly developed, so that the endocrine therapy of breast cancer is now taking a new turn.

As progesterone receptor antagonist to be used as oral contraceptives or breast cancer treating drugs, RU38486 (Cancer Res., vol. 49, pp. 2851–2856, 1989) and ZK98299 and ZK112993 (J. Sterold Biochem. Molec. Biol., vol. 41, pp. 339–348, 1992) are now under development. Since these agents still have problems in terms of side effect or production cost and their effects are not satisfied, the development of a new progesterone receptor antagonist has been desired in accordance with the increase in incidence of drug-resistant breast cancers.

SUMMARY OF THE INVENTION

In view of the above, the present inventors have continued screening of substances which inhibit binding of progesterone to progesterone receptor and have found that substances, which inhibit binding of progesterone to progesterone receptor, are produced in a cultured mixture of a strain belonging to the genus Penicillium. And the present inventors have isolated a substance PF1092A, a substance PF1092B and a substance PF1092C as active ingredients from the cultured mixture, and thereby completed the present invention.

The object of the present invention is to provide novel physiologically active substances PF1092A, PF1092B and PF1092C, or salts thereof, and a process for their production.

Figure 1:
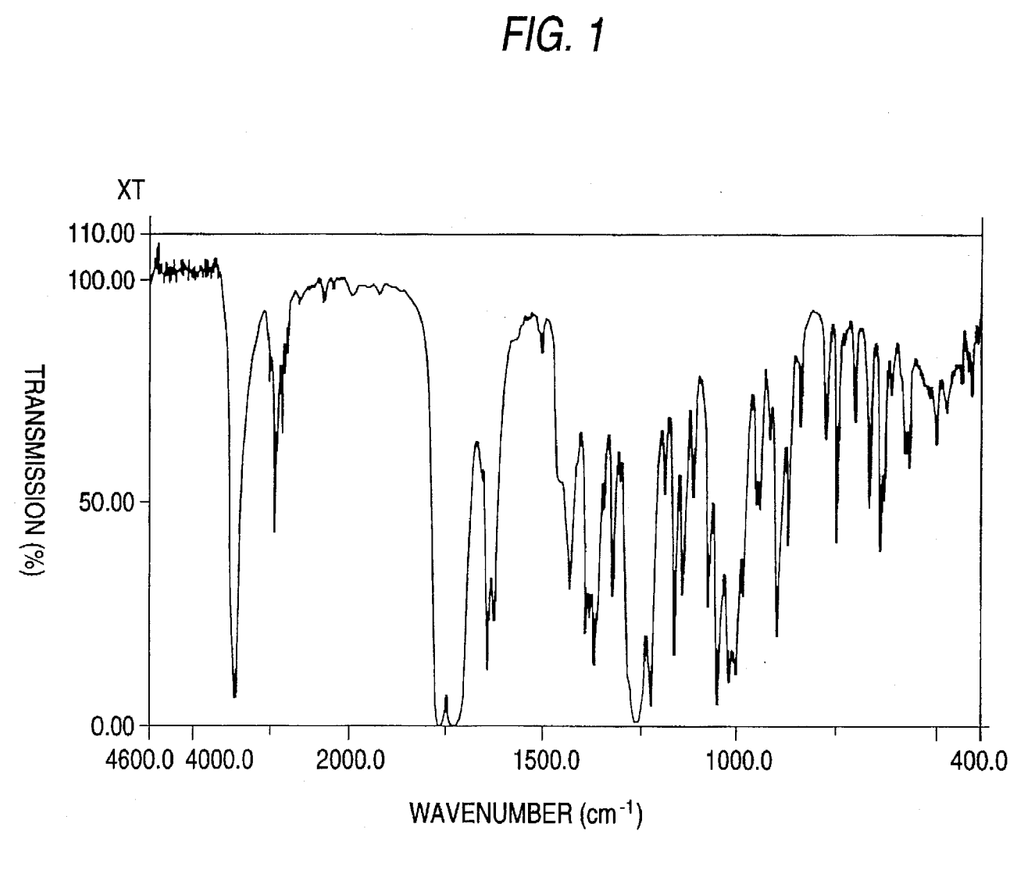
FIG. 1 is a graph showing infrared absorption spectrum of substance PF1092A in KBr tablet.
Figure 2:
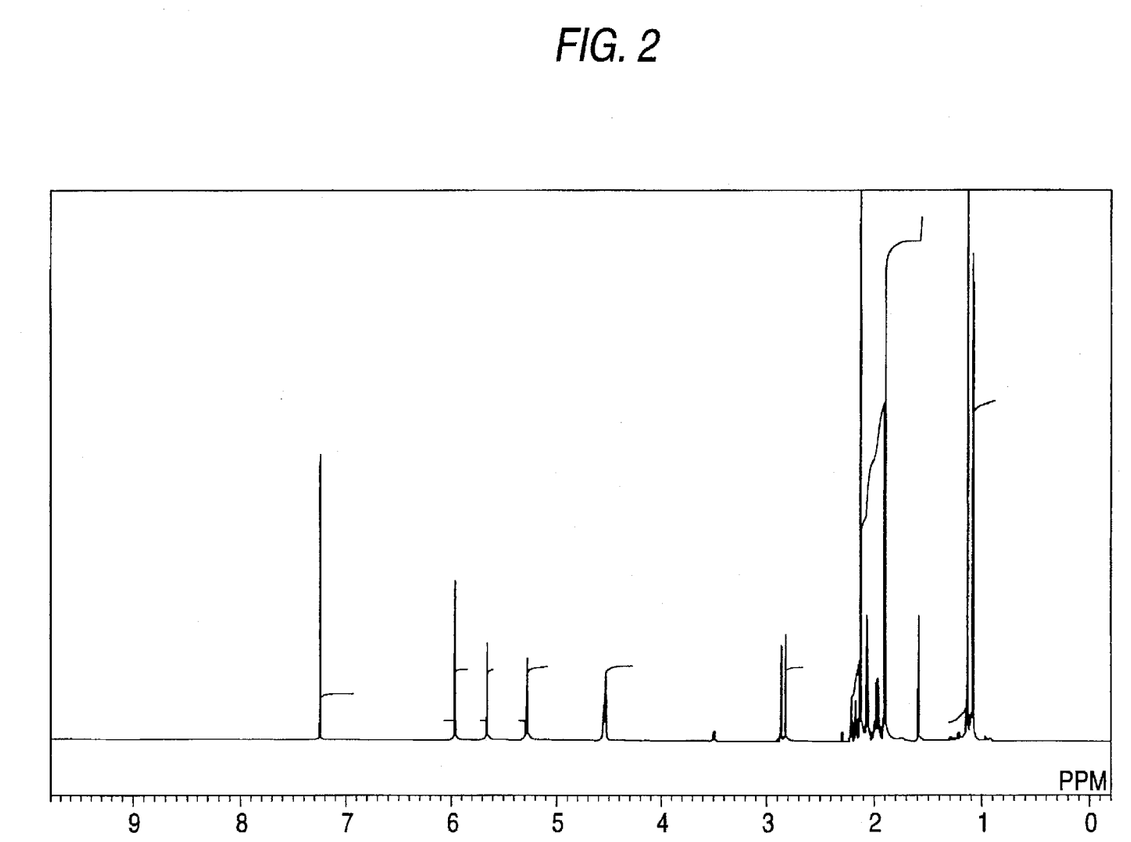
FIG. 2 is a graph showing 400 MHz $^1H$ NMR spectrum of substance PF1092A in $CDCl_3$ solution.
Figure 3:
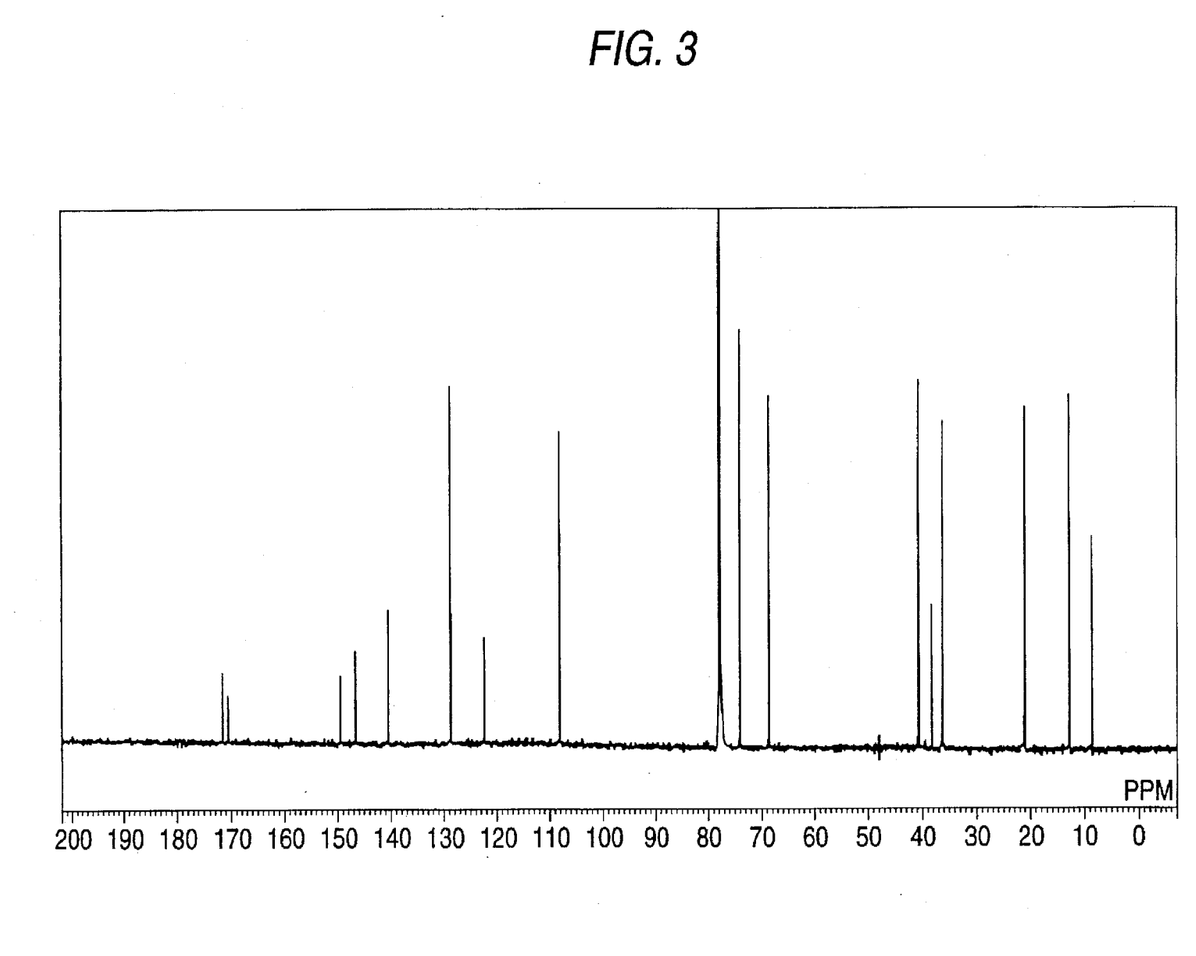
FIG. 3 is a graph showing 100 MHz $^{13}C$ NMK spectrum of substance PF1092A in $CDCl_3$ solution.

The first aspect of the present invention relates to a substance PF1092A which has the following physico-chemical properties:

(1) color and shape: colorless needle crystals;
(2) molecular formula: $C_{17}H_{20}O_5$;
(3) mass spectrum (FD-MS): m/z 304 $(M)^+$;
(4) specific rotation: $[\alpha]_D = -10.86°$ ($\underline{c}$ 0.5, $CHCl_3$);
(5) ultraviolet ray absorption spectrum λmax: 322 (17, 500) nm(ε) (in methanol);
(6) infrared absorption spectrum: measured in KBr tablet, as Shown in FIG. 1;
(7) $^1H$ NMR spectrum: measured in $CDCl_3$ solution, as shown in FIG. 2
  δ (ppm): 5.97 (1H), 5.66 (1H), 5.28 (1H), 4.53 (1H), 2.83 (1H), 2.19 (3H), 2.18 (1H), 2.05 (0H), 1.97 (1H), 1.91 (3H), 1.15 (3H), 1.10 (3H);
(8) $^{13}C$ NMR spectrum: measured in $CDCl_3$ solution, as shown in FIG. 3
  δ (ppm): 171.8 (s), 170,9 (s), 149.3 (s), 146.3 (s), 140.4 (s), 128.7 (d), 122,3 (s), 107.7 (d), 73.6 (d), 68.2 (d), 40.2 (d), 37.8 (s), 35.6 (t), 21.0 (q), 20,9 (q), 12.7 (q), 8.6 (q);
(9) solubility: soluble in chloroform, acetone, ethyl acetate, methanol and dimethyl sulfoxide, and insoluble in water and hexane;
(10) basic, acidic or neutral: neutral substance; and
(11) Rf value by silica gel thin layer chromatography (TLC): 0.25 in hexane-ethyl acetate (1:1) developing solvent.

Figure 4:
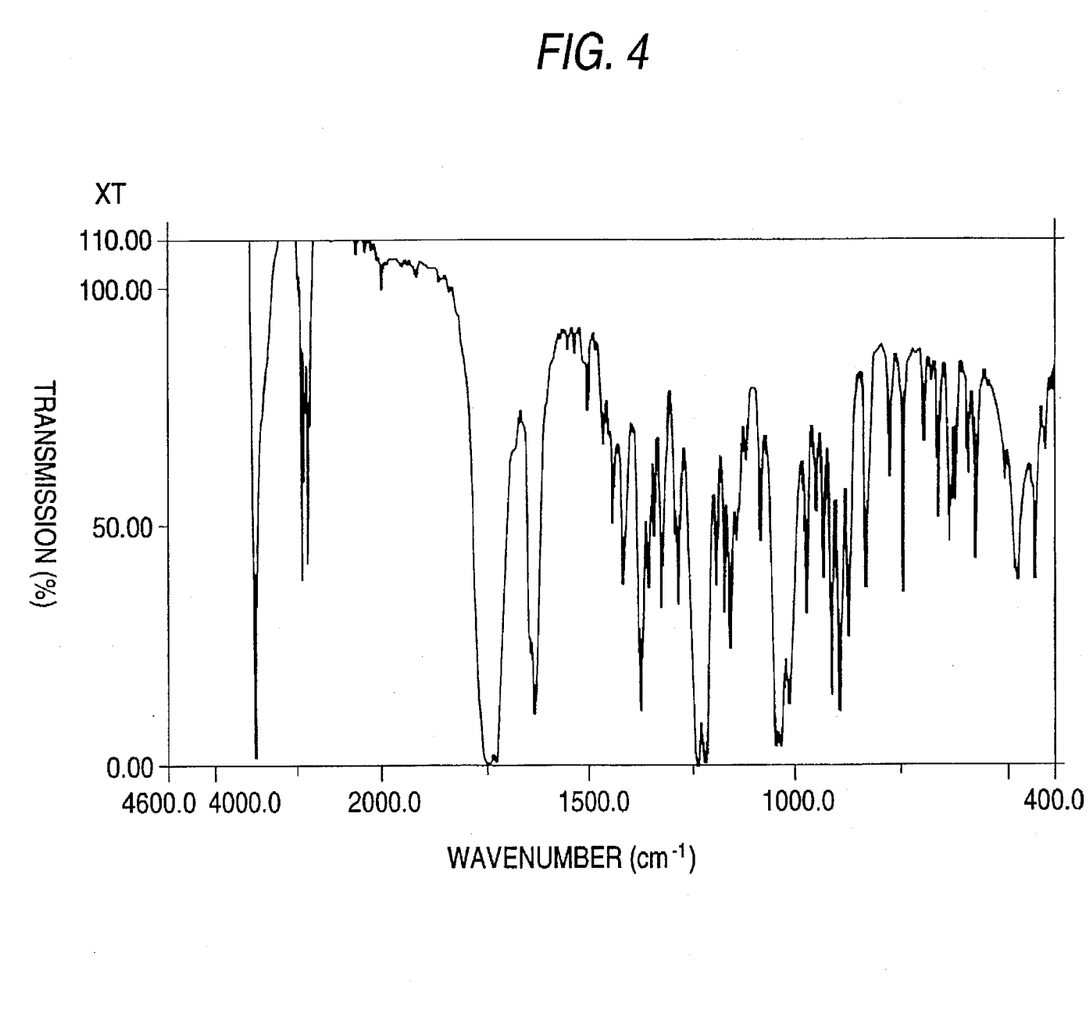
FIG. 4 is a graph showing infrared absorption spectrum of substance PF1092B in KBr tablet.
Figure 5:
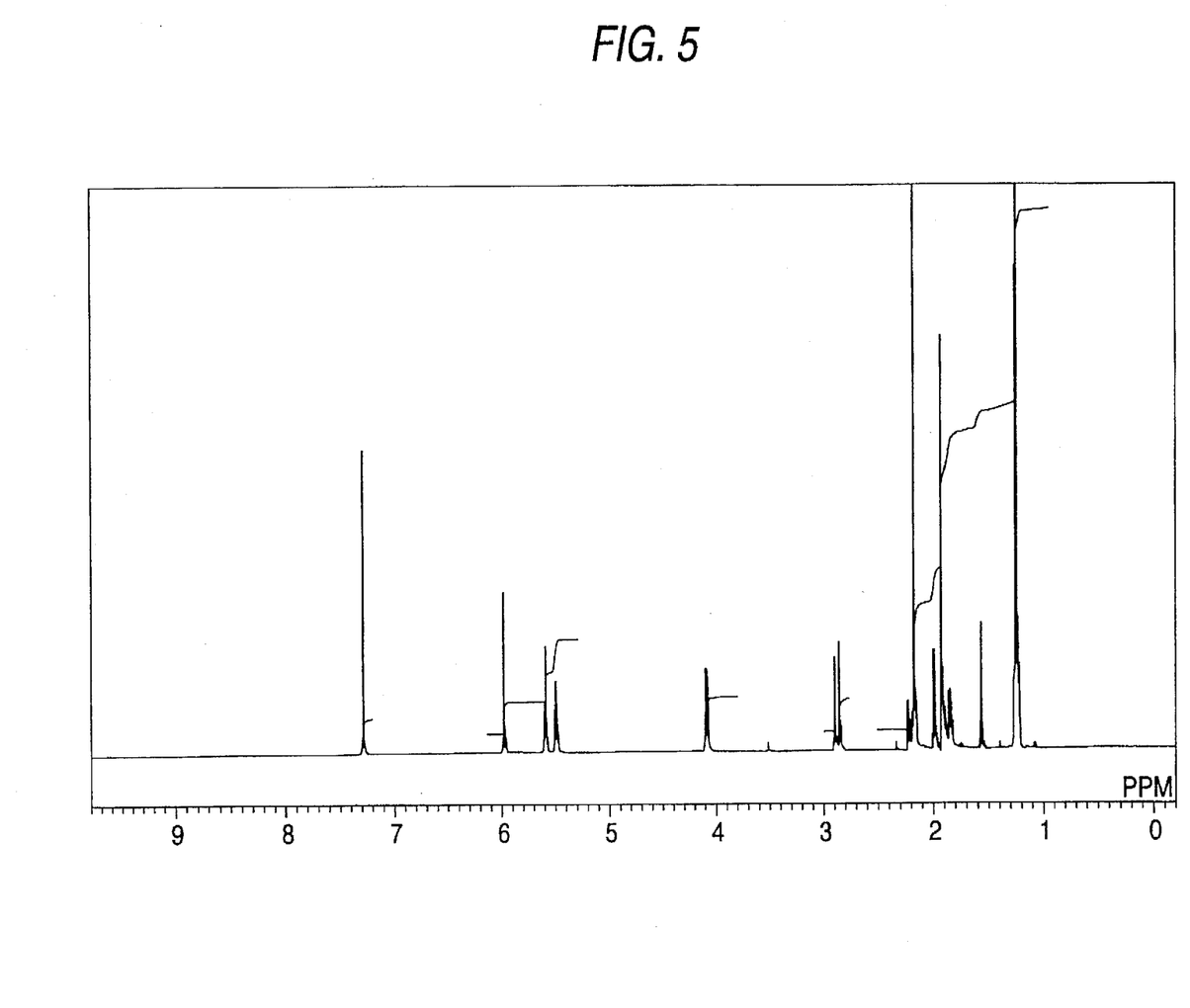
FIG. 5 is a graph showing 400 MHz $^1H$ NMR spectrum of substance PF1092B in $CDCl_3$ solution.
Figure 6:
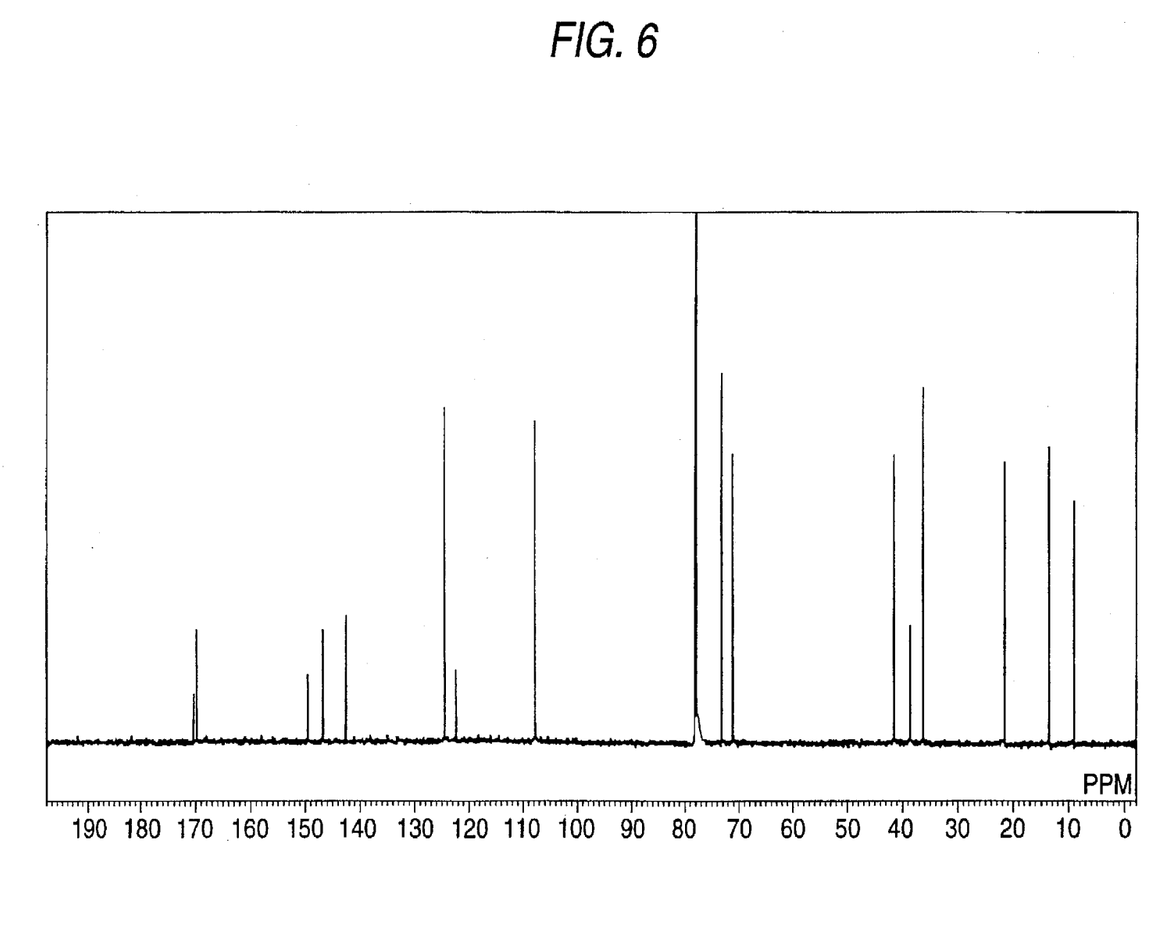
FIG. 6 is a graph showing 100 MHz $^{13}C$ NMR spectrum of substance PF1092B in $CDCl_3$ solution.

The second aspect of the present invention relates to a substance PF1092B which has the following physico-chemical properties:

(1) color and shape: colorless needle crystals;
(2) molecular formula: $C_{17}H_{20}O_5$;
(3) mass spectrum (FD-MS): m/z 304 $(M)^+$;
(4) specific rotation: $[\alpha]_D = -110.22°$ ($\underline{c}$ 0.5, $CHCl_3$);
(5) ultraviolet ray absorption spectrum λmax: 320 (15, 100) nm(ε) (in methanol);
(6) infrared absorption spectrum: measured in KBr tablet, as shown in FIG. 4;
(7) $^1H$ NMR spectrum: measured in $CDCl_3$ solution, as shown in FIG. 5
  δ (ppm): 5.95 (1H), 5.57 (1H), 5.46 (1H), 4.05 (1H), 2.84 (1H), 2.18 (1H), 2.15 (3H), 1.97 (0H), 1.91 (3H), 1.83 (1H), 1.23 (3H), 1.22 (3H);
(8) $^{13}C$ NMR spectrum: measured in $CDCl_3$ solution, as shown in FIG. 6
  δ (ppm): 170.9 (s), 170.2 (s), 149.5 (s), 146.7 (s), 142.4 (s), 124.5 (d), 122.4 (s), 107.4 (d), 72.5 (d), 70.5 (d), 41.0 (d), 38.1 (s), 35.8 (t), 21.4 (q), 21.2 (q), 12.8 (q), 8.6 (q);
(9) solubility: soluble in chloroform, acetone, ethyl acetate, methanol and dimethyl sulfoxide, and insoluble in water and hexane;
(10) basic, acidic or neutral: neutral substance; and
(11) Rf value by silica gel thin layer chromatography (TLC): 0.42 in hexane-ethyl acetate (1:1) developing solvent.

Figure 7:
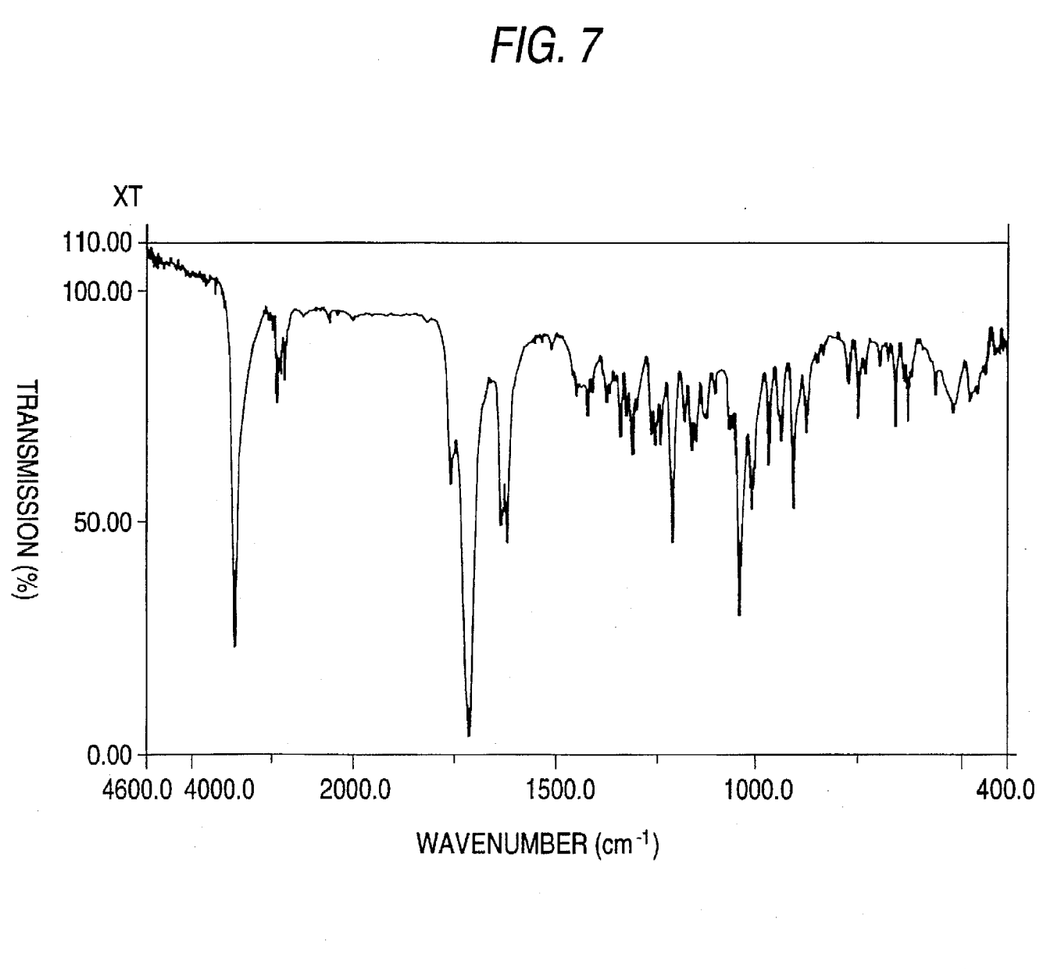
FIG. 7 is a graph showing infrared absorption spectrum of substance PF1092C in KBr tablet.
Figure 8:
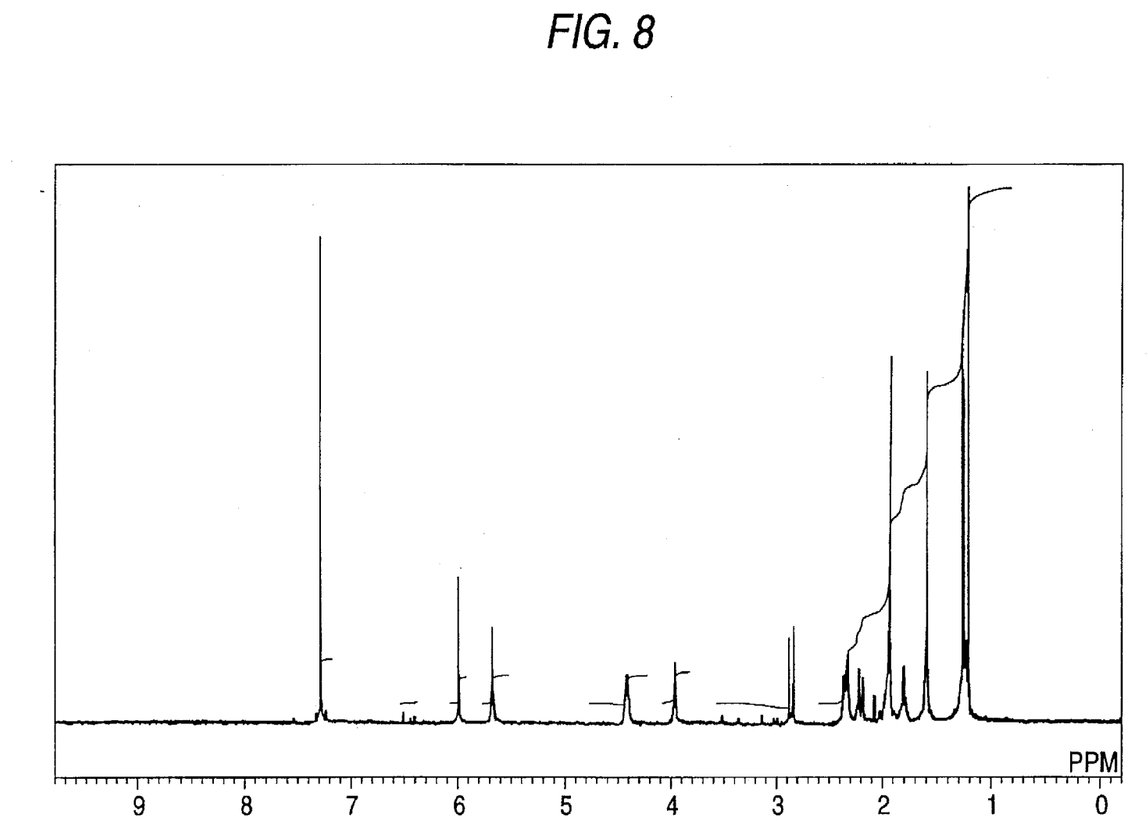
FIG. 8 is a graph showing 400 MHz $^1H$ NMR spectrum of substance PP1092C in $CDCl_3$ solution.
Figure 9:
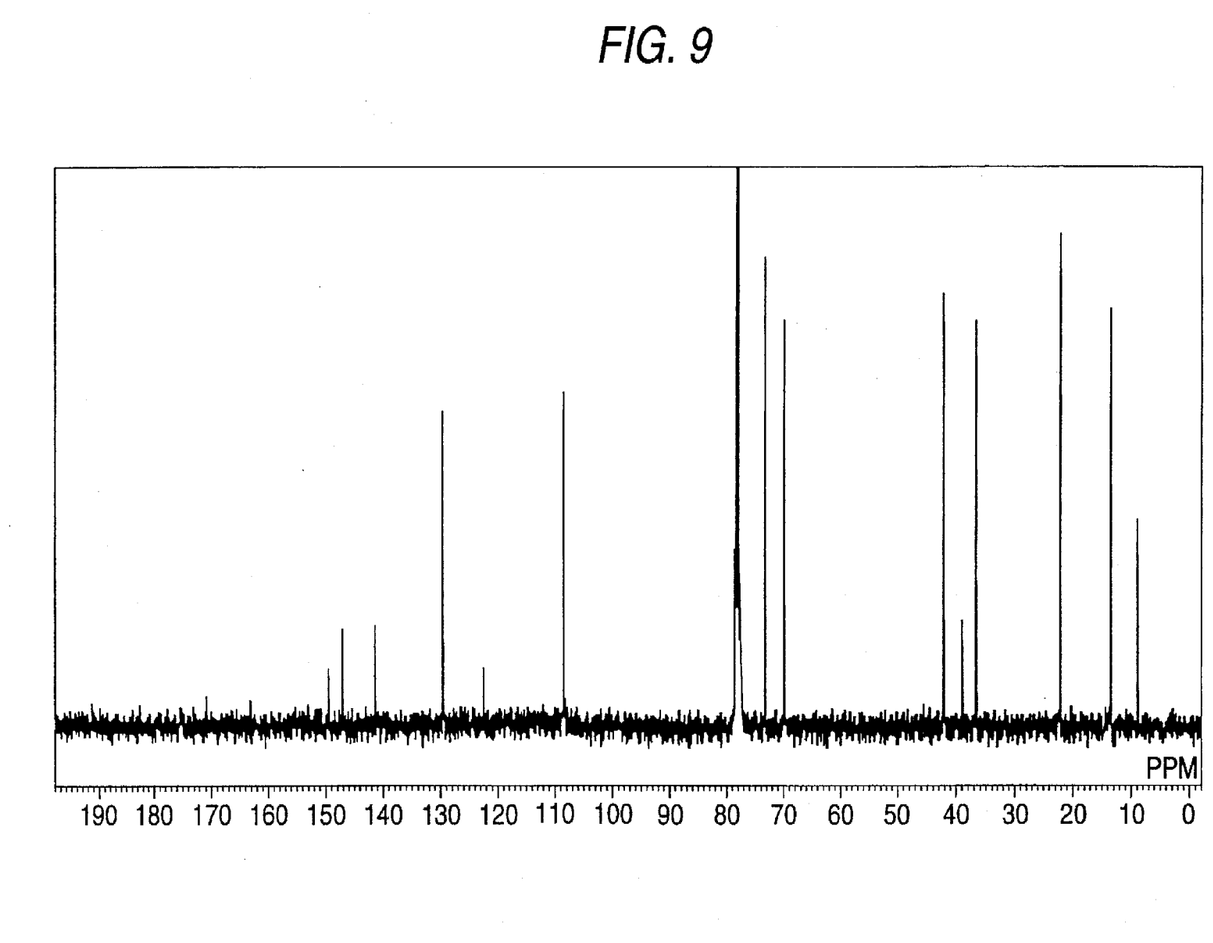
FIG. 9 is a graph showing 100 MHz $^{13}C$ NMR spectrum of substance PF1092C in $CDCl_3$ solution.

The third aspect of the present invention relates to a substance PF1092C which has the following physico-chemical properties:

(1) color and shape: colorless needle crystals;

(2) molecular formula: $C_{15}H_{18}O_4$;

(3) mass spectrum (FD-MS): m/z 262 $(M)^+$;

(4) specific rotation: $[\alpha]_D=-96.36°$ (c 0.5, $CHCl_3$);

(5) ultraviolet ray absorption spectrum λmax: 324 (14, 900) nm(ε) (in methanol);

(6) infrared absorption spectrum: measured in KBr tablet, as shown in FIG. 7;

(7) $^1H$ NMR spectrum: measured in $CDCl_3$ solution, as shown in FIG. 8

δ (ppm): 5.96 (1H), 5.64 (1H), 4.37 (1H), 3.93 (1H), 2.83 (1H), 2.22 (0H), 2.20 (0H), 2.17 (1H), 1.91 (3H), 1.24 (3H), 1.20 (3H);

(8) PC NMR spectrum: measured in $CDCl_3$ solution, as shown in FIG. 9

δ (ppm): 171.0 (s), 149.3 (s), 146.7 (s), 141.0 (s), 129.1 (d), 122.1 (s), 107.8 (d), 72.4 (d), 69.0 (d), 40.3 (d), 37.9 (s), 35.9 (t), 21.5 (q), 13.0 (q), 8.5 (q);

(9) solubility: soluble in chloroform, acetone, ethyl acetate, methanol and dimethyl sulfoxide, and insoluble in water and hexane;

(10) basic, acidic or neutral: neutral substance; and (11) Rf value by silica gel thin layer chromatography (TLC): 0.20 in hexane-ethyl acetate (1:1) developing solvent.

The fourth aspect of the present invention relates to a process for producing a physiologically active substance PF1092 which comprises culturing a fungal microorganism capable of producing the physiologically active substances PF1092 and collecting the physiologically active substances PF1092 from the cultured mixture. Strain PF1092 to be used in the present invention is a fungus isolated from a soil sample collected in 1991.

Other objects and advantages of the present invention will be made apparent as the description progresses.

DETAILED DESCRIPTION OF THE INVENTION

1. Mycological properties of strain PF1092

(1) Cultural characteristics:

It forms a colony of 30 to 40 mm diameter on Czapek yeast extract agar medium after culturing at 25° C. for 7 days. The colony is white and funiculose, and forms conidia scatteringly. Backside of the colony becomes light brown. It grows well on malt extract agar medium, and diameter of its colony reaches 40 to 45 mm after culturing at 25° C. for 7 days. The colony is white and funiculose, forms conidia slightly and produces light brown extract. Backside of the colony becomes light mud yellow. At 37° C., its growth and formation of conidia are superior to those at 25° C. on all media.

(2) Morphological characteristics:

Conidiophore stands straight almost vertically from aerial mycelium, is rough-surfaced and has a size of 30–70× 2.5–3.5 μm. Penicilli are monoverticillate. Four to eight phialides are formed on conidiophore, each being needle-like and having smooth to slightly rough surface and a size of 8–10×2.5–3.0 μm. Conidium is globose to subglobose, flat with slightly depressed sides, and has smooth surface and a size of 2.0–2.5μm.

On the basis of the above mycological characteristics, this strain was identified as the genus Penicillium.

This strain has been deposited in National Institute of Bioscience and Human Technology, Agency of Industrial Science and Technology, as FERM P-14724 (international deposition number under Budapest Treaty, FERM BP-5350).

As can be found in other fungi, strain PF1092 is apt to change its properties. For example, not only strain PF1092 but also all of its mutant strains (spontaneous or induced mutants), zygotes and genetic recombinants can be used in the present invention, provided that they can produce substances PF1092.

2. A method of culturing substance PF1092 producing strain

The substance PF1092 producing strain is cultured using a medium containing nutrients which can be utilized by ordinary microorganisms. As the nutrient sources, known materials conventionally used for the culturing of fungi can be used. Examples of usable carbon sources include glucose, sucrose, starch syrup, dextrin, starch, glycerol, molasses, animal and plant oils and the like. Examples of usable nitrogen sources include soybean meal, wheat germ, corn steep liquor, cotton seed meal, meat extract, peptone, yeast extract, ammonium sulfate, sodium nitrate, urea and the like. In addition to these nutrients, it is effective to add inorganic salts which can release sodium, potassium, calcium, magnesium, cobalt, chlorine, phosphate, sulfate and the like ions as occasion demands. Also, certain organic and inorganic substances which can assist the fungal growth and enhance the production of substances PF1092 may be added properly.

Preferably, the culturing may be carried out under aerobic Conditions, particularly by static culturing using a rice medium or by submerged culturing. Suitable culturing temperature is 15° to 40° C., but the culturing is carried out at about 26° to 37° C. in most cases. Though it varies depending on the medium and culturing conditions employed, accumulation of produced substances PF1092 reaches its maximum generally after 10 to 20 days of culturing in the case of static culturing using a rice medium or generally after 2 to 10 days of shaking or fermentor culturing. The culturing is completed when maximum accumulation of substances PF1092 is obtained, and the desired substance is isolated and purified from the culture broth.

3. Purification of substances PF1092

Substances PF1092 thus obtained by the present invention can be extracted and purified from the cultured mixture making use of its properties by usual separation means such as solvent extraction, ion exchange resin method, absorption or partition chromatography, gel filtration, dialysis, precipitation and the like, alone or in an appropriate combination. For example, substances PF1092 can be extracted with acetone-water or ethyl acetate after culturing using a rice medium. In order to further purify substances PF1092, a chromatography may be carried out using an adsorbent such as silica gel (for example, Wakogel C-200 manufactured by Wako Pure Chemical Industries), alumina or the like or Sephadex LH-20 (manufactured by Pharmacia), Toyo Pearl HW-40SF (manufactured by Tosoh) or the like.

By carrying out such techniques alone or in an optional combination, highly purified substance PF1092A, substance PF1092B and substance PF1092C are obtained. Physico-chemical properties and chemical structures of the thus obtained substances PF1092A, PF1092B and PF1092C are as follows.

1. Physico-chemical properties and chemical structure of substance PF1092A:

(1) Color and shape: colorless needle crystals
(2) Molecular formula: $C_{17}H_{20}O_5$
(3) Mass spectrum (FD-MS): m/z 304 $(M)^+$
(4) Specific rotation: $[\alpha]_D = -10.86°$ (c 0.5, $CHCl_3$)
(5) Ultraviolet ray absorption spectrum λmax: 322 (17, 500) ran(e) (in methanol)
(6) Infrared absorption spectrum: measured in KBr tablet (see FIG. 1)
(7) $^1$H NMR Spectrum: measured in $CDCl_3$ solution (see FIG. 2)
  δ (ppm): 5.97 (1H), 5.66 (1H), 5.28 (1H), 4.53 (1H), 2.83 (1H), 2.19 (3H), 2.18 (1H), 2.05 (0H), 1.97 (1H), 1-91 (3H), 1.15 (3H), 1.10 (3H)
(8) $^{13}$C NMR Spectrum: measured in $CDCl_3$ solution (see FIG. 3)
  δ (ppm): 171.8 (s), 170.9 (s), 149.3 (s), 146.3 (s), 140.4 (s), 128.7 (d), 122.3 (s), 107.7 (d), 73.6 (d)r 68.2 (d), 40.2 (d), 37.8 (s), 25.6 (t), 21.0 (q), 20.9 (q), 12.7 (q), 8.6 (q)
(9) Solubility: soluble in chloroform, acetone, ethyl acetate, methanol and dimethyl sulfoxide, and insoluble in water and hexane
(10) Basic, acidic or neutral: neutral substance
(11) Rf Value by silica gel thin layer chromatography (TLC): 0.25 in hexane-ethyl acetate (1:1) developing solvent

Based on the above physico-chemical properties and X-ray crystallographic analysis, the following chemical structure was determined.

(I)

2. Physico-chemical properties and chemical structure of substance PF1092B:

(1) Color and shape: colorless needle crystals
(2) Molecular formula: $C_{17}H_{20}O_5$
(3) Mass spectrum (FD-MS): m/z 304 $(M)^+$
(4) Specific rotation: $[\alpha]_D^{24} = -110.22°$ (c 0.5, $CHCl_3$)
(5) Ultraviolet ray absorption spectrum λmax: 320 (15, 100) nm(e) (in methanol)
(6) Infrared absorption spectrum: measured in KBr tablet (see FIG. 4)
(7) $^1$H NMR Spectrum: measured in $CDCl_3$ solution (see FIG. 5)
  δ (ppm): 5.95 (1H), 5.57 (1H), 5.46 (1H), 4.05 (1H), 2.84 (1H), 2.18 (1H), 2,15 (3H), 1.97 (0H), 1.91 (3H), 1.83 (1H), 1.23 (3H), 1.22 (3H)
(8) $^{13}$C NMR Spectrum: measured in $CDCl_3$ solution (see FIG. 6)
  δ (ppm): 170.9 (e), 170.2 (G), 149.5 (s), 146.7 (s), 142.4 (s), 124.5 (d), 122.4 (s), 107.4 (d), 72.5 (d), 70.5 (d), 41.0 (d), 38.1 (s), 35.8 (t), 21.4 (q), 21.2 (q), 12.8 (q), 8.6 (q)
(9) Solubility: soluble in chloroform, acetone, ethyl acetate, methanol and dimethyl sulfoxide, and insoluble in water and hexane
(10) Basic, acidic or neutral: neutral substance
(11) Rf Value by silica gel thin layer chromatography (TLC): 0.42 in hexane-ethyl acetate (1:1) developing solvent

Based on the above physico-chemical properties and X-ray crystallographic analysis, the following chemical structure was determined.

(II)

3. Physico-chemical properties and chemical structure of substance PF1092C:

(1) Color and shape: colorless needle crystals
(2) Molecular formula: $C_{15}H_{18}O_4$
(3) Mass spectrum (FD-MS): m/z 262 $(M)^+$
(4) Specific rotation: $[\alpha]_D^{24} = -96.3°$ (c 0.5, $CHCl_3$)
(5) Ultraviolet ray absorption spectrum λmax, 324 (14, 900) nm(e) (in methanol)
(6) Infrared absorption spectrum: measured in KBr tablet (see FIG. 7)
(7) $^1$H NMR Spectrum: measured in CDCls solution (see-FIG. 8)
  δ (ppm): 5.96 (1H), 5.64 (1M), 4.37 (1H), 3.93 (1M), 2.83 (1H), 2.22 (0H), 2.20 (0H), 2.17 (1H), 1.91 (3H), 1.24 (3H), 1.20 (3H).
(8) $^{13}$C NMR Spectrum: measured in $CDCl_3$ solution (see FIG. 9)
  δ (ppm): 171.0 (s), 149.3 (s), 146.7 (s), 141.0 (s), 129.1 (d), 122.1 (s), 107.8 (d), 72.4 (d), 69.0 (d), 40.3 (d), 37.9 (s), 35.8 (t), 21.5 (q), 13.0 (q), 8.5 (q).
(9) Solubility: soluble in chloroform, acetone, ethyl acetate, methanol and dimethyl sulfoxide, and insoluble in water and hexane,
(10) Basic, acidic or neutral: neutral substance
(11) Rf Value by silica gel thin layer chromatography (TLC): 0.20 in hexane-ethyl acetate (1:1) developing solvent.

Based on the above physico-chemical properties and X-ray crystallographic analysis, the following chemical structure was determined.

(III)

Examples of the salts of substances PP1092 include metal salts, particularly alkali metal salts such as sodium salt and alkaline earth metal salts such as calcium salt, as well as acid addition salts with pharmaceutically acceptable inorganic or organic acids.

As described below, the substance PF1092A, substance PF1092B and substance PF1092C or salts thereof in the present invention are Useful as contraceptives or anticancer drugs. When used as pharmaceutical preparations, various known formulation and administration methods can be employed. The drug compositions of the present invention are prepared by using substance PF1092A, substance PF1092B and substance PF1092C or salts thereof as active ingredients, mixing them with usually used inorganic or organic carriers and then making the mixture into solid, semi-solid or liquid form to give oral preparations or parenteral preparations such as external preparations.

Examples of the dosage form for use in oral administration include tablets, pills, granules, soft or hard capsules, powders, fine subtilaes, dusts, emulsions, suspensions, syrups, pellets, elixirs and the like. Examples of the dosage form for use in parenteral administration include injections, drip infusion, transfusion, ointments, lotions, tonic preparations, sprays, suspensions, oils, emulsions, suppositories and the like. Formulation of the active ingredients of the present invention can be effected in accordance with an ordinary method by optionally using surface active agents, fillers, coloring agents, flavors, preservatives, stabilizers, buffers, suspending agents, tonicity agent's and other usually used adjuvants.

Dose of the drug composition of the present invention varies depending on its type, diseases to be treated or prevented, its administration method, age and symptoms of each patient, treating period and the like, but, in general, the active ingredient may be administered in a dose per day per adult of from 0.01 to 1,000 mg/kg, preferably from 0.1 to 100 mg/kg in the case of intravenous injection, from 0,01 to 1,000 mg/kg, preferably from 0.1 to 100 mg/kg in the case of intramuscular injection or from 0.5 to 2,000 mg/kg, preferably from 1 to 1,000 mg/kg in the case one oral administration.

The following examples are provided to further illustrate the present invention. However, since various methods for the production of substances PF1092 can be devised based on its properties revealed by the present invention, it is to be expressly understood that the examples are not intended as a definition of the limits of the invention and therefore that not only modification means of the examples but also all methods for the production, concentration, extraction and purification of substances PF1092 carried out by known means based on its properties revealed by the present invention are included in the present invention. In these examples, all the percente are given by weight unless otherwise indicated.

INVENTIVE EXAMPLE 1

A medium composed of 2.0% of starch, 1.0% of glucose, 0.5% of polypeptone, 0.6% of wheat germ, 0.3% of yeast extract, 0.2% of soybean meal and 0.2% of calcium carbonate (pH 7,0 before sterilization) was used as a seed culture medium. Another medium prepared by adding 0.3% of soybean meal to sufficiently water-absorbed rice was used as a production medium.

A 20 ml portion of the seed culture medium dispensed in a 100 ml capacity conical flask was sterilized at 120° C. for 15 minutes, and one loopful of Penicillium sp. PF1092 (FERM P-14724) cells grown on a slant agar medium were inoculated into the medium and cultured at 25° C. for 3 days on a shaker to obtain a seed culture. Next, a 100 g portion of the aforementioned production medium dispensed in a 500 ml capacity conical flask was sterilized at 120° C. for 15 minutes, and 5 ml of the just obtained seed culture was inoculated into the medium, mixed thoroughly and then subjected to 10 days of static culturing at 28° C.

INVENTIVE EXAMPLE 2

A 6 kg portion of the thus obtained culture mixture was extracted with 12 liters of ethyl acetate, and the resulting ethyl acetate layer containing active components was evaporated to obtain 15.3 g of oily material. The thus obtained oily material was applied to a column packed with 400 g of silica gel (Wakogel C-200, manufactured by Wako Pure Chemical Industries), washed with chloroform and then chromatographed using chloroform-methanol (100:1 to 100:3) as a developing solvent, and the resulting active fraction was evaporated to obtain 4.6 g of crude powder. Next, the crude powder was applied to a column packed with 150 g of silica gel (Wakogel C-200, manufactured by Wako Pure Chemical Industries), washed with hexane-ethyl acetate (8:1 to 5:1) and then chromatographed using hexane-ethyl acetate (4:1 to 3:1) as a developing solvent to effect elution of substance PF1092B, and the resulting active fraction was evaporated to obtain 282 mg of crude powder containing substance PF1092B. The chromatography was continued using hexane-ethyl acetate (2:1 to 1:1) as a developing solvent to effect elution of substance PF1092A and substance PF1092C, and the resulting active fraction was evaporated to obtain 763 mg of crude powder containing substance PF1092A and substance PF1092C. Next, the crude powder containing substance PF1092B was purified by Sephadex LH-20 (700 ml, manufactured by Pharmacia) column chromatography using chloroform-methanol (1:1) as a developing solvent, and the active fraction containing substance PF1092B was evaporated to obtain 157.0 mg of substance PF1092B as colorless powder. The colorless powder of substance PF1092B was then dissolved in a chloroform-methanol mixture and allowed to stand to obtain 49.1 mg of substance PF1092B as colorless needle crystals.

On the other hand, the crude powder containing substance PF1092A and substance PF1092C obtained by the silica gel column chromatography using hexane-ethyl acetate (2:1 to 1:1) as a developing solvent was purified by Sephadex LH-20 (700 ml) column chromatography using chloroform-methanol (1:1) as a developing solvent to obtain 298 mg of substance PF1092A as colorless powder and then 159 mg of substance PF1092C as colorless powder. Thereafter, the colorless powder of substance PF1092A was dissolved in a chloroform-methanol mixture and allowed to stand to obtain 60.0 mg of substance PF1092A as colorless needle crystals, and the Colorless powder of substance PF1092C was dissolved in ethyl acetate and allowed to stand to obtain 30.1 mg of substance PF1092C as colorless needle crystals.

These substances have the aforementioned physicochemical properties.

TEST EXAMPLE

The progesterone receptor binding activity of substance PF1092A, substance PF1092B and substance PF1092C of the present invention was measured in the following manner in accordance with the method of H. Kondo et al. (*J. Antibiotics*, vol. 43, pp. 1533–1542, 1990). That is, uteri taken from hogs in 5 mM phosphate buffer were disrupted using Polytron homogenizer, and the resulting solution was subjected to centrifugation (100,000 ×g, 30 minutes) to separate the supernatant fluid which was used as the cytosol containing progesterone receptor.

In the assay of progesterone receptor binding activity, 40 μl of a solution of $^3$H-progesterone as a ligand of the receptor (3.84 TBq/mmol, 18.5 kBq/ml), 50 μl of the just obtained cytosol (2–3 mg protein/ml), 30 μM of substance PF1092A, substance PF1092B and substance PF1092C and 30 μM of medroxyprogesterone acetate (MPA) were put into a test tube and incubated at 4° C. for 60 minutes to effect the reaction and then mixed with 100 μl of 0.5% activated carbon solution. After 10 minutes of standing, this was subjected to centrifugation (2,000×g, 10 minutes), and radioactivity of the thus obtained supernatant fluid was measured using a liquid scintillation counter. Inhibition ratio was calculated based on the following formula in which radioactivity with no addition of the test drug was defined as the amount of total binding to the cytosol and radioactivity with the addition of MPA was defined as the amount of non-specific binding.

$$\text{Inhibition ratio} = \left\{1 - \frac{\text{(total binding amount with test drug added)} - \text{(non-specific binding amount)}}{\text{(total binding amount with no test drug added)} - \text{(non-specific binding amount)}}\right\} \times 100$$

As the results, 30 μM of each of substance PF1092A and substance PF1092B inhibited 90% or more of the binding of $^3$H-progesterone to the progesterone receptor. At the same concentration, substance PF1D92C inhibited about 70% of the binding. On the basis of the above results, it was confirmed that substance PF1092A, substance PF1092B and substance PF1092C are capable of binding to the progesterone receptor.

Thus, the substance PF2092A, substance PF1092B and substance PF1092C of the present invention can inhibit binding of progesterone to the progesterone receptor. On the basis of this property, the substance PF1092A, substance PF1092B and substance PF1092C of the present invention can be used as contraceptives or anticancer drugs, or lead compounds from which more effective derivatives will be synthesized.

While the invention has been described in detail and with reference to specific embodiments thereof, it will be apparent to one skilled in the art that various changes and modifications can be made therein without departing from the spirit and scope thereof.

What is claimed is:

1. A compound represented by formula (A):

wherein $R^1$ is an acetyl group and $R^2$ is a hydrogen atom; $R^1$ is a hydrogen atom and $R^2$ is an acetyl group; or $R^1$ is a hydrogen atom and $R^2$ is a hydrogen atom.

2. The compound of claim 1 wherein $R^1$ is an acetyl group and $R^2$ is a hydrogen atom.

3. The compound of claim 1 wherein $R^1$ is a hydrogen atom and $R^2$ is an acetyl group.

4. The compound of claim 1 wherein $R^1$ is a hydrogen atom and $R^2$ is a hydrogen atom.

5. A pharmaceutical composition comprising at least one physiologically active substance represented by formula (A):

wherein $R^1$ is an acetyl group and $R^2$ is a hydrogen atom; $R^1$ is a hydrogen atom and $R^2$ is an acetyl group; or $R^1$ is a hydrogen atom and $R^2$ is a hydrogen atom, or a pharmaceutically acceptable salt thereof as an active ingredient, together with a pharmaceutically acceptable carrier.

* * * * *